United States Patent [19]

Sigl et al.

[11] 4,437,860

[45] Mar. 20, 1984

[54] DISPOSABLE DIAPER WITH ELASTICIZED LEG OPENINGS

[75] Inventors: Wayne C. Sigl; Richard H. Frick, both of Neenah, Wis.

[73] Assignee: Kimberly-Clark Corporation, Neenah, Wis.

[21] Appl. No.: 294,843

[22] Filed: Aug. 21, 1981

[51] Int. Cl.³ .............................................. A41B 13/02
[52] U.S. Cl. ..................................................... 604/385
[58] Field of Search ................ 128/284, 287; 604/385

[56] References Cited

U.S. PATENT DOCUMENTS

| | | | |
|---|---|---|---|
| 4,205,679 | 6/1980 | Repke et al. | 128/287 |
| 4,259,958 | 4/1981 | Goodbar | 128/287 |
| 4,325,372 | 4/1982 | Teed | 128/287 |
| 4,326,528 | 4/1982 | Ryan et al. | 128/287 |
| 4,333,782 | 6/1982 | Pieniak | 128/287 |

*Primary Examiner*—C. Fred Rosenbaum
*Attorney, Agent, or Firm*—Richard C. Ruppin

[57] ABSTRACT

A disposable diaper with uniformly stretched elastic bands adhesively bonded along the entire length of both edges of the diaper with heavier concentrations of adhesive in the waistband portions than in the crotch portion to reduce gathering and creep of the elastic in the waistband portions. Preferably the diaper is of hour glass shape with the elastic outboard of the absorbent batt in the crotch portion and extending across the laterally extending ears of the absorbent batt in the waistband portions to further improve the stability thereof.

7 Claims, 3 Drawing Figures

DISPOSABLE DIAPER WITH ELASTICIZED LEG OPENINGS

FIELD OF THE INVENTION

The present invention relates generally to disposable diapers and the like and more particularly concerns disposable diapers with elasticized leg openings.

BACKGROUND OF THE INVENTION

Disposable diapers with elasticized leg openings are known in the art. Buell U.S. Pat. No. 3,860,003 discloses one form of such a diaper, which is made in accordance with the teaching in Buell U.S. Pat. No. 4,081,301. Another form of elastic legged diaper is disclosed in Woon et al. U.S. Pat. No. 4,050,462. These patents teach that the elastic material in the waistband area should be free of adhesives so that the elastic does not exert a retractive force in this portion of the diaper. On the other hand, Bourgeois U.S. Pat. No. 3,828,367 discloses a disposable panty-like garment wherein the elastic is uniformly stretched and adhered to the garment along its entire length. Gore U.S. Pat. No. 4,239,578 also discloses a disposable diaper wherein the elastic is adhered to the diaper along its entire length but the elastic in the waistband is relaxed or unstretched relative to the elastic in the leg opening area. Other elastic legged disposable diapers are disclosed in copending Sigl U.S. application Ser. No. 094,421, filed Nov. 15, 1979; Ryan et al. U.S. application Ser. No. 135,255, filed Apr. 4, 1980; and Frick U.S. application Ser. No. 181,821, filed Aug. 27, 1980, all three of which applications are assigned to the asignee of the present application. Still other examples of elasticized diapers are disclosed in British application Nos. GB 2010628A and GB 2011778A; Australian application No. 43750/79; South African application No. 77/4456; and U.S. Pat. No. 4,227,952.

SUMMARY OF THE INVENTION

According to the present invention, uniformly stretched elastic bands are adhesively bonded along the entire length of both edges of a disposable diaper with heavier concentrations of adhesive being applied to the elastic in the waistband portion of the diaper than in the leg opening area to substantially decrease the retractive force of the stretched elastic in the waistband area thereby reducing gathering thereof and diminishing undesirable creep.

BRIEF DESCRIPTION OF THE DRAWINGS

These and other objects and advantages of the present invention will become more readily apparent upon reading the following detailed description and upon reference to the attached drawings, in which.

While the invention will be described in connection with certain preferred embodiments and procedures, it will be understood that we do not intend to limit the invention to those specific embodiments and procedures. On the contrary, we intend to cover all alternatives, modifications and equivalents as may be included within the spirit and scope of the invention as defined by the appended claims.

DETAILED DESCRIPTION OF THE INVENTION

Figure 1:
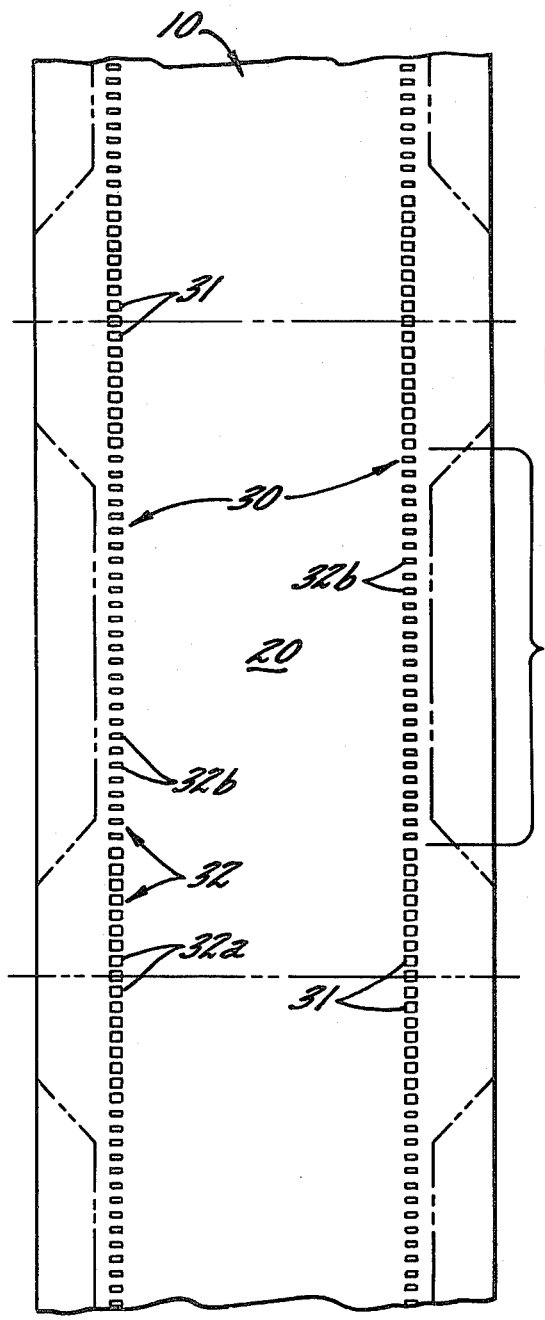
FIG. 1 is a plan view of a web of diaper material, from which individual diapers are subsequently cut, with stretched elastic bands, continuously adhered along the length of the web and having heavier concentrations of adhesive adhering the elastic to the web in those areas of the web which will become the waistband portion of the diapers.
Figure 2:
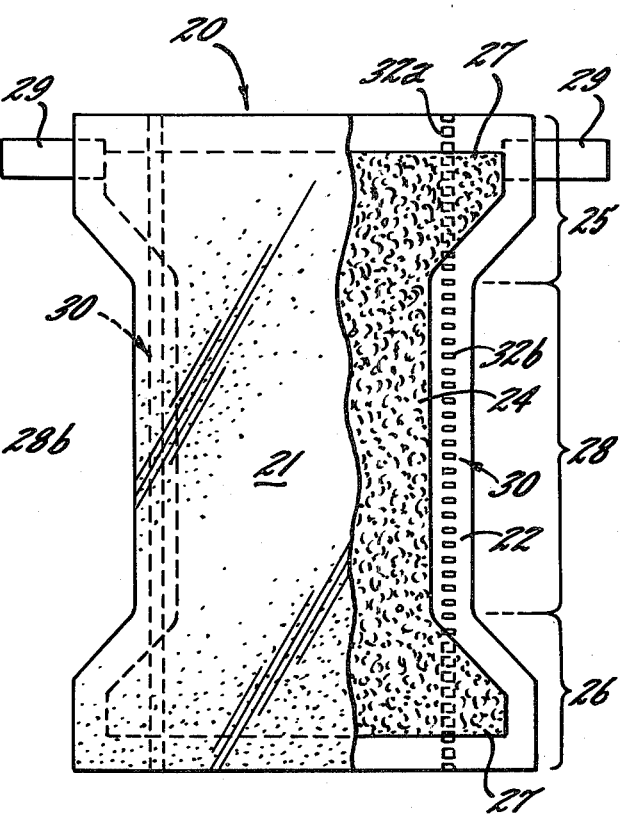
FIG. 2 is a plan view of a completed diaper, with portions broken away for clarity of illustrations, cut from the web but prior to retraction of the elastic bands.

Turning now to the drawings, the present invention has been illustrated in connection with the formation of a conformable garment which is shown as a disposable diaper, generally indicated at 20. Although the exemplary diaper 20 is illustrated in FIG. 2 in the form of a finished product severed from a continuous web 10 of products as shown in FIG. 1 made in a high speed continuous production operation, it has, for purposes of facilitating a complete understanding of the invention, nevertheless been shown in FIG. 2 in the stretched or fully extended position that the product would normally occupy just prior to being severed from the continuous web 10 upon completion of the manufacturing process.

In keeping with the present invention, the illustrative diaper 20 is of elongate generally "I" shape, and includes a fluid permeable facing sheet 21, a fluid impervious backing sheet 22, and a highly absorbent batt 24 sandwiched between the facing and backing sheets 21, 22 respectively.

The specific components used to form the exemplary diaper may be any of the types commonly used for such purposes. For example, the fluid pervious facing sheet may be any soft, flexible porous sheet which permits the passage of fluids therethrough including hydrophobic or hydrophilic nonwoven webs, wet strength papers, spunwoven filament sheets, and the like. A particularly suitable sheet is one made of spunwoven polypropylene filaments with spot embossing, and preferably with a perforated surface or suitable surfactant treatment to aid fluid transfer.

The fluid impermeable backing sheet 22 is preferably a thin plastic film such as polyethylene, polypropylene, polyvinylchloride, or the like and would generally be on the order of one mil in thickness. The sheet is preferably opaque with an embossed or matte surface. A suitable material for the absorbent batt 24 used in the exemplary diaper is an air-formed batt of wood pulp fibers commonly known as "fluff". Other absorbent materials, alone or in combination and including webs of carded or air-laid textile fibers, multiple plys of creped cellulose wadding, various super absorbent materials, sythetic foam sheets or the like may also be used. The batt may also be slightly compressed or embossed in selected areas as desired.

The exemplary diaper shown in FIG. 2 is divided into waistband sections 25 and 26 at each end and a central narrowed-down crotch section 28 disposed between the waistband sections. During use, waistband section 25 would normally be disposed at the back of the infant and may from time to time be referred to herein as the back portion of the diaper, while section 26 would normally be disposed at the front and may from time to time be referred to herein as the front portion of the diaper. Conventional pressure sensitive tapes 29 are attached to the backing sheet 22 near the edges of waistband section 25 for fastening purposes, although other suitable fastening means may be employed. Such tapes are usually attached near the back portion of the diaper.

One surface of absorbent batt 24 is secured to backing sheet 22 and/or to facing sheet 21 in at least the crotch section 28. Preferably, the absorbent batt is bonded to backing sheet 22 in the crotch section. Such bonding may be done by the use of strips of double-faced pressure sensitive tape, by strips of hot melt or pressure sensitive adhesive, by overall or patterned heat sealing, by a printed pattern of adhesives, or the like. One desirable type of adhesive is an atactic polypropylene based hot melt adhesive of the type known as A337S manufactured by Eastman Chemical Co. of Kingsport, Tenn.

Each edge of the diaper 20 in the narrow crotch section 28 is provided with an elongate elastic means 30 secured in extended condition to backing sheet 22 and/or to facing sheet 21 along the entire length of the diaper 20. In keeping with the present invention, the ends 31 of the elastic means 30 positioned in the waistband sections 25, 26 are provided with heavier concentrations of adhesive in such a manner as to substantially lessen their elastic properties relative to the backing sheet 22.

As previously indicated, the elastic means 30 is fully stretched and under tension only during the manufacturing process when it exists as a continuous length for convenience in the process. As noted, the diaper is shown in the drawings in its fully extended condition, a condition which it would normally occupy only during the manufacturing process when a series of diapers 20 are attached to each other in the form of a continuous strip or web 10. When this continuous web 10 is cut into individual diapers 20, the elastic means 30 is thus relieved of its tension and contracts from its fully extended condition, causing the crotch section 28 of the diaper to contract in the elasticized area. As indicated above, however, the waistband sections 25 and 26 are essentially not constricted and remain substantially flat or planar because the end portions 31 of the elastic means 30 do not exhibit strong elastic characteristics relative to the underlying backing sheet 22 and, consequently, there is a general absence of tensioned elastic in those sections.

When the relatively narrow crotch section 28 is constricted by the contracted elastic means 30 at each edge, the crotch section may develop a multiplicity of gross transverse rugosities as disclosed in Woon et al. U.S. Pat. No. 4,050,462 and copending Ryan et al. U.S. application Ser. No. 135,255, which are incorporated herein by reference. Suffice it to say, crotch section 28 is reduced in length but still contains the same amount of absorbent material. Accordingly, the absorbent batt 24 in the crotch area 28 is made effectively thicker because of the adjoining hills and valleys of which the transverse rugosities are comprised and, therefore, will have more absorbent capacity per unit area than a batt of the same original thickness has in its initial planar form. In addition to making the diaper 20 effectively more absorbent in the crotch area 28, the cushioning effect of the pad element forming the rugosities serves to relieve some of the pressure of the tensioned elastic means 30 where it presses the diaper into contact with the infant's skin when the diaper is worn.

Pursuant to the present invention, the adhesive is applied to the elastic means in the form of a generally brick-shaped pattern formed of a multiplicity of bars 32 of adhesive. In the preferred embodiment, the adhesive bars are applied by an adhesive print roll directly to the stretched elastic just prior to it being bonded to the fluid impervious backing sheet 22. It will be understood, however, that the elastic could be bonded to the fluid permeable facing sheet 21 and, also, the adhesive could be printed on facing sheet 21 and/or backing sheet 22 and then the stretched elastic adhered thereto.

In further accordance with the invention, heavier concentrations of adhesives are applied to the ends 31 of the elastic means 30 then to the central portions thereof in the crotch section 28 of the diaper. Accordingly, the adhesive bars 32a in the waistband portions 25, 26 are wider and spaced closer together than the adhesive bars 32b in the crotch portion 28 of the diaper. (See area 28b in FIG. 1). The heavier concentrations of adhesive provided by wider bars 32a serve to substantially stabilize the stretched elastic and to greatly reduce its retractive force in the waistband portions 25, 26 of the diaper. The result is that the tendency of the waisband portions 25, 26 to gather is significantly reduced as compared to the crotch portions 28. It will also be appreciated that the ear-shaped portions 27 at the ends of the absorbent batt 24 extend laterally outboard of the ends 31 of the elastic means 30 and these ears 27 contribute to the stiffening of waistband portions 25, 26 of the diaper. Indeed, the combination of the backing sheet 22, adhered elastic 30, absorbent pad ears and facing sheet 21 in laminar fashion provide waistband portions 25, 26 which have little tendency to gather or pucker up.

Figure 3:
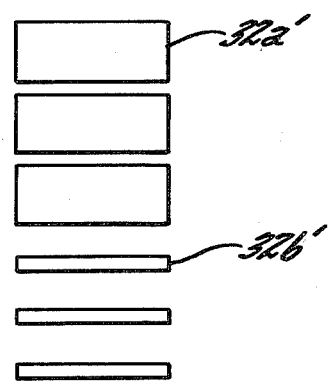
FIG. 3 is an enlarged fragmentary plan view of a portion of a print roll pattern for applying adhesive bars to the elastic strips.

FIG. 3 shows an enlarged, fragmentary view of the print roll pattern for applying the wide bars 32a and narrow bars 32b of adhesive to the elastic strips 30. In one example, the wide bars 32a' on the print roll have a nominal width of about 13/32 inch and a nominal spacing of about 1/32 inch between bars. The narrow bars 32b' on the print roll may have a nominal width of about 3/32 inch and a spacing of about ¼ inch. In other words, the wide bars 32a may be on the order of about four times as wide as the narrow bars 32b and the narrow bars 32a may be spaced about 8–10 times farther apart than the wide bars 32a. Because the elastic is under some tension as it leaves the print roll, the width of the bars 32a, 32b and the space between them tends to increase slightly, desirably only about 5% or less. The length of the bars 32a and 32b in the transverse direction of the diaper should be at least equal to the width of the stretched elastic 30 to ensure holding of the elastic. Moreover, a length of the bars 32a and 32b exceeding the width of the elastic 30 is desirable to ensure adherence even though the elastic 30 deviates laterally during adherence.

One type of adhesive that has been found satisfactory for practicing the present invention is a hot melt ethylene vinyl acetate (eva) material, such as HM-1342 made by the H. B. Fuller Company. Another hot melt adhesive which may be used is a block copolymer material such as HM-1533A (styrene-butadiene-styrene-triblock polymer) also made by the H. B. Fuller Company. The eva type adhesive, when set, is relatively stiff and imparts somewhat greater rigidity to the waistband portions 25, 26 than does the block copolymer type material. On the other hand, the block copolymer adhesive is somewhat more flexible and provides a waistband portion with greater conformability.

It will be appreciated, of course, that other adhesive formulations can be employed without departing from the present invention. The adhesive should be of a quick setting type in order to stabilize the stretched elastic and prevent "creep" which is the tendency of the elastic to separate from the material to which it is adhered.

We claim as our invention:

1. In a disposable diaper having an absorbent batt interposed between a fluid permeable facing sheet and a fluid impervious backing sheet and having a generally hour glass shape with a narrow centrally disposed crotch portion and wider waistband portions at the ends thereof, the improvement comprising, prestretched elastic means extending along the length of the diaper at each side, said elastic disposed outboard of the absorbent batt in the crotch portion and across the laterally extending ears of the absorbent batt in the waistband portions of the diaper, adhesive means for securing said elastic to at least one of said facing sheet and backing sheet substantially along the entire length of said diaper, said adhesive being applied in the form of longitudinally spaced apart concentrations, said concentrations in the waistband portion being substantially larger and more closely spaced than said concentrations in the crotch portions of the diaper to substantially decrease the retractive force of the stretched elastic in the waistband portions to thereby reduce gathering thereof and diminish undesirable elastic creep.

2. A disposable diaper as defined in claim 1 wherein said adhesive is applied in the form of a multiplicity of laterally extending bars.

3. A disposable diaper as defined in claim 2 wherein said adhesive is applied to said prestretched elastic.

4. A disposable diaper as defined in claim 2 wherein said adhesive is applied to said backing sheet.

5. A disposable diaper as defined in claim 2 wherein said adhesive is applied to said facing sheet.

6. A disposable diaper as defined in claim 2 wherein the bars in the waistband portion are about four times as wide as the bars in the crotch portion.

7. A disposable diaper as defined in claim 2 wherein said laterally extending bars are substantially rectangular in shape and the length of the bar exceeds the width of the elastic so as to ensure the adherence of the elastic over its entire width.

* * * * *